US00PP11287P

United States Patent [19]

Stackman

[11] Patent Number: Plant 11,287

[45] Date of Patent: Mar. 14, 2000

[54] PAGODA DOGWOOD NAMED 'WSTACKMAN'

[76] Inventor: Walter Stackman, 28 W. 609 Boles, West Chicago, Ill. 60185

[21] Appl. No.: 08/959,838

[22] Filed: Oct. 29, 1997

[51] Int. Cl.[7] ..... A01H 5/00

[52] U.S. Cl. ..... Plt./220

[58] Field of Search ..... Plt./53.2, 220

[56] References Cited

U.S. PATENT DOCUMENTS

P.P. 9,283 9/1995 Schmidt ..... Plt./53.2

OTHER PUBLICATIONS

The New Royal Horticultural Society Dictionary of Gardening, Ed.–in–Chief Anthony Huxley, Stockton Press, New York, p. 723, 1992.

*Primary Examiner*—Howard J. Locker
*Assistant Examiner*—Anne Marie Grünberg
*Attorney, Agent, or Firm*—C. A. Whealy

[57] ABSTRACT

A new and distinct cultivar of Pagoda Dogwood plant named 'Wstackman', characterized by its vigorous growth rate and large leaves with unique green and yellow variegated foliage.

3 Drawing Sheets

BACKGROUND OF THE INVENTION

The present invention relates to a new and distinct cultivar of Pagoda Dogwood, botanically known as *Cornus alternifolia*, and hereinafter referred to by the cultivar name Wstackman.

The new Pagoda Dogwood was discovered by the Inventor in a cultivated area in West Chicago, Ill., as a naturally-occurring branch sport of a plant of an unnamed variety of *Cornus alternifolia*. This unnamed variety is described as having solid green (nonvariegated) leaves. The selection of this branch sport was based on its unique variegated foliage.

Asexual reproduction of the new Pagoda Dogwood by terminal cuttings harvested in West Chicago, Ill., and Grand Haven, Mich., has shown that the unique features of this new Pagoda Dogwood are stable and reproduced true to type in successive generations.

BRIEF SUMMARY OF THE INVENTION

Plants of the new Pagoda Dogwood have not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Wstackman'. The characteristics in combination distinguish 'Wstackman' as a new and distinct cultivar:

1. Vigorous growth rate.

2. Large leaves with unique green and yellow variegated foliage.

The new Pagoda Dogwood differs from the parent variety of *Cornus alternifolia* primarily in leaf coloration as plants of the new Pagoda Dogwood have variegated leaves whereas plants of the parent variety have nonvariegated, solid green, leaves.

The new Pagoda Dogwood can be compared to the variegated *Cornus alternifolia* cultivar Argentea, not patented. In side-by-side comparisons conducted by the Inventor in West Chicago, Ill., plants of the new Pagoda Dogwood differed from plants of the cultivar Argentea in the following characteristics:

1. Plants of the new Pagoda Dogwood have much larger and flatter (less puckered) leaves than plants of the cultivar Argentea.

2. Plants of the new Pagoda Dogwood are more vigorous and stronger than plants of the cultivar Argentea.

3. Leaf variegation of plants of the new Pagoda Dogwood is more stable than plants of the cultivar Argentea as plants of the cultivar Argentea occasionally exhibit solid green leaves.

4. The color of the leaf variegation is dissimilar as plants of the new Pagoda Dogwood have green and yellowish-colored variegation whereas plants of the cultivar Argentea have green and grayish white-colored variegation.

BRIEF DESCRIPTION OF THE PHOTOGRAPHS

The accompanying colored photographs illustrate the overall appearance of the new Pagoda Dogwood, showing the colors as true as it is reasonably possible to obtain in colored reproductions of this type.

The photograph on the first sheet comprises a close-up view of a typical variegated leaf and a typical flower of the new Pagoda Dogwood.

The photographs on the second and third sheets comprise face views of typical specimens of the new Pagoda Dogwood. Foliage and flower colors in the photographs may appear different from the actual colors due to light reflectance.

DETAILED BOTANICAL DESCRIPTION

The following observations, measurements, values, and comparisons describe plants grown in West Chicago, Ill., and Grand Haven, Mich., under outdoor conditions which closely approximate commercial production conditions. Plants used for this description were about three years old and grown in 28-cm containers.

In the following description, color references are made to The Royal Horticultural Society Colour Chart except where general terms of ordinary dictionary significance are used.

Botanical classification: *Cornus alternifolia* cultivar Wstackman.

Parentage: Naturally-occurring branch sport of unnamed variety of *Cornus alternifolia* described as having solid green (nonvariegated) leaves.

Propagation:

*Type*.—By terminal softwood cuttings.

*Time to initiate roots in the summer*.—About 20 days at temperatures of about 27° C.

*Time to develop roots in the summer*.—About 35 days at temperatures of about 27° C.

*Rooting habit*.—Fleshy.

Plant description:

*Plant form and growth habit*.—Perennial deciduous tree, mostly upright with horizontal branching.

*Vigor*.—Vigorous, similar to plants of the parent variety.

*Plant size*.—A two-year old plant will attain a height of about 75 cm and a width of about 40 cm under outdoor Northern Illinois conditions. Mature trees will achieve a height and width of about 6 meters after about 10 years.

*Branching habit*.—Moderate, branch crotch angles of about 60° to main trunk.

*Main stem, or trunk, description*.—Diameter: About 2 cm. Internode length: About 10 to 15 cm. Bark texture: Smooth. Bark color: Red purple, close to 59A, with gray, close to 201A, lenticels.

*Lateral branch description*.—Diameter: About 3 to 6 mm. Internode length: About 10 to 15 cm. Texture: Smooth. Color: Red purple, close to 59A.

Foliage description:

*Arrangement*.—Simple, alternate; leaves mostly crowded towards branch apices.

*Length*.—About 9 cm.

*Width*.—About 6 cm.

*Petiole length*.—About 4.5 cm.

*Petiole diameter*.—About 2.5 mm.

*Shape*.—Ovate to elliptic.

*Apex*.—Acuminate.

*Base*.—Cuneate.

*Margin*.—Entire, slightly undulate.

*Texture*.—Upper surface: Nearly glabrous. Lower surface: Minute hairs pressed to surface.

*Color*.—Continuous center of the leaf, green, surrounded by yellowish green to grayed yellow area that extends to the leaf margin. Actual variegation pattern is variable. Occasional green blotches may randomly appear in the yellowish outer leaf area. Variegation patterns will be expressed on both surfaces of the leaves. Young leaves, upper surface: Center, medium green, 146C; outer variegated area, light yellowish green, 151C. Young leaflets, lower surface: Similar to upper surface, but dulled. Mature leaves, upper surface: Center, dark green, 146C; outer variegated area, yellowish green, 153C. With increasing light levels during the late spring and summer or under full sunlight, the color of the yellowish green portion of the leaf will become grayed yellow, 160B/162C. In the early spring and in the fall, a pinkish red hue becomes evident on the outer variegated area and becomes deeper pink with cooler temperatures. Mature leaves, lower surface: Similar to upper surface, but dulled. Petiole: Pinkish red.

Flower description: Flowers typical of species.

*Natural flowering season*.—Late Spring.

*Inflorescence arrangement*.—Flowers arranged in terminal cymes; 4-merous; subtended by a corolla-like involucre of showy bracts.

*Inflorescence diameter*.—About 6 cm.

*Inflorescence depth*.—About 3.5 cm.

*Involucral bracts*.—Diameter: About 3 to 3.5 cm. Shape: Ovate to oblong. Upper surface: Close to 155D or slightly creamy. Lower surface: Close to 155D or slightly creamy.

*Sepals*.—Typically four, minute.

*Stamens*.—Typically four; exserted.

*Pistil*. —Typically one; stigma, capitate.

*Ovary*.—Inferior: 2-celled; densely pubescent.

Fruit description:

*Type*.—Fruits are 2-celled, 2-seeded drupes.

*Shape*.—Globose.

*Diameter*.—About 6 to 8 mm.

*Color*.—Deep bluish black, close to 103A.

*Seed*.—Obovoid, shallowly channeled.

Disease resistance: Resistance to diseases common to plants of Pagoda Dogwood has not been observed under outdoor conditions.

It is claimed:

1. A new and distinct Pagoda Dogwood plant named 'Wstackman', as illustrated and described.

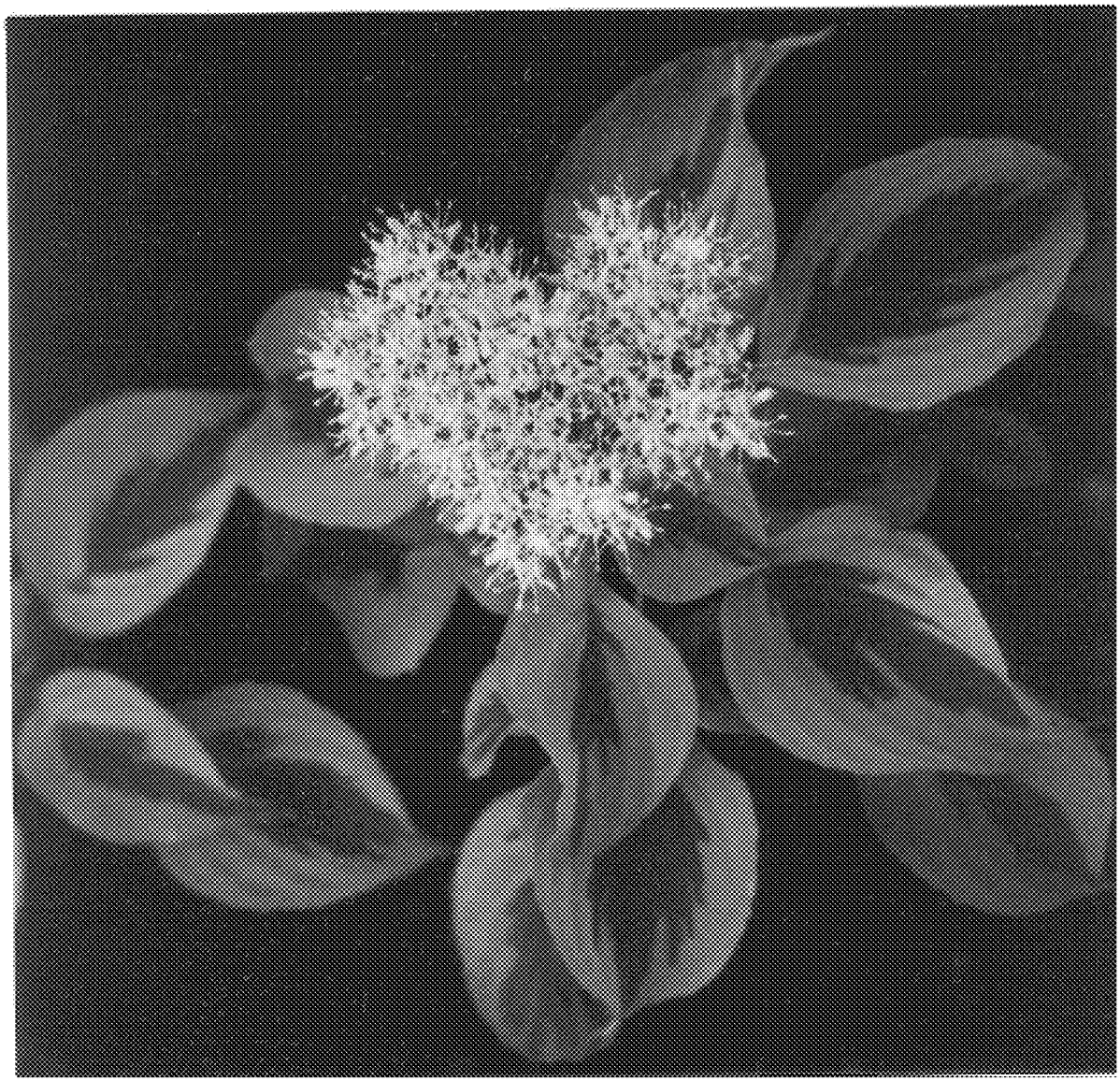

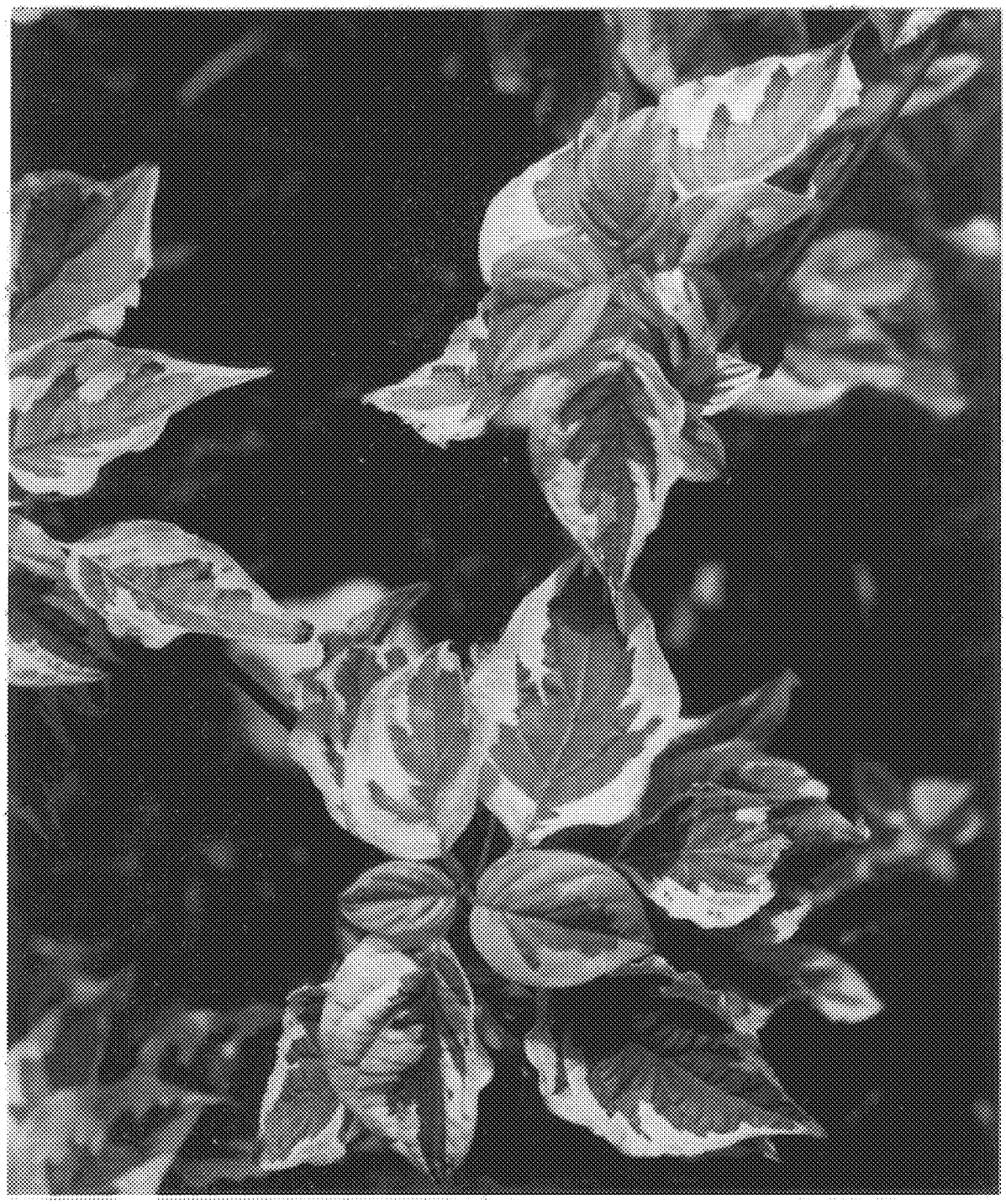

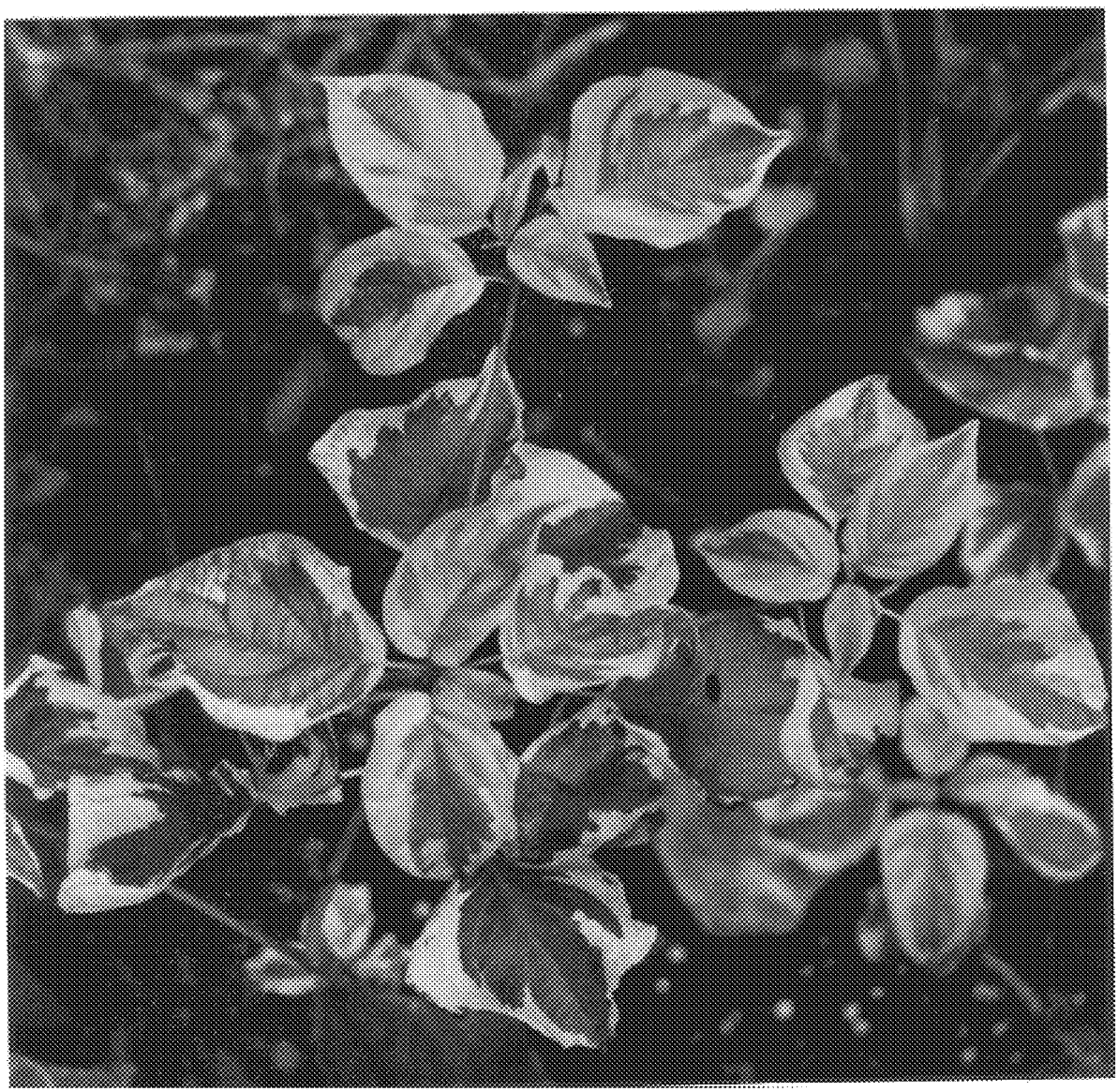

* * * * *